United States Patent
Wilkening et al.

(10) Patent No.: US 9,398,898 B2
(45) Date of Patent: Jul. 26, 2016

(54) MULTIPLE BEAM SPECTRAL DOPPLER IN MEDICAL DIAGNOSTIC ULTRASOUND IMAGING

(75) Inventors: Wilko Wilkening, Mountain View, CA (US); Saurabh Datta, Cupertino, CA (US); Paul Freiburger, Seattle, WA (US); Chi-Yin Lee, Bellevue, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 654 days.

(21) Appl. No.: 13/032,834

(22) Filed: Feb. 23, 2011

(65) Prior Publication Data
US 2012/0215110 A1 Aug. 23, 2012

(51) Int. Cl.
*A61B 8/06* (2006.01)
*A61B 8/08* (2006.01)
*G01S 7/52* (2006.01)
*A61B 8/00* (2006.01)

(52) U.S. Cl.
CPC .............. *A61B 8/488* (2013.01); *A61B 8/5246* (2013.01); *G01S 7/5209* (2013.01); *G01S 7/52066* (2013.01); *G01S 7/52088* (2013.01); *G01S 7/52095* (2013.01); *A61B 8/06* (2013.01); *A61B 8/463* (2013.01); *A61B 8/486* (2013.01); *A61B 8/5223* (2013.01); *G01S 7/52092* (2013.01); *G01S 7/52093* (2013.01)

(58) Field of Classification Search
None
See application file for complete search history.

(56) References Cited

U.S. PATENT DOCUMENTS 5,365,929 A * 11/1994 Peterson ................. 600/456
5,993,390 A * 11/1999 Savord et al. ............. 600/437
(Continued)

FOREIGN PATENT DOCUMENTS

EP 1 462 819 9/2004
WO WO 00/57768 10/2000

OTHER PUBLICATIONS

Lewis et al., Pulsed Doppler echocardiographic determination of stroke volume and cardiac output: clinical validation of two new methods using the apical window, Circulation 1984, vol. 70, No. 3, pp. 425-431.*

(Continued)

*Primary Examiner* — Long V Le
*Assistant Examiner* — Bradley Impink (57) ABSTRACT

Spatially distinct Spectral Doppler information is acquired. Spatially distinct transmit beams are formed at a same time or in parallel. One or more receive beams are formed in response to each transmit beam, providing samples for a plurality of laterally spaced locations. A spectrum is determined for each of a plurality of spatial locations. In another approach, samples are acquired for different regions at different times. The scanning for each region is interleaved based on the anatomic operation. Since spectral estimation relies on a time-continuous series of transmission and reception, the scanning for a region occurs over a sufficient period for spectral estimation before the scanning for a different region occurs. By using anatomic operation, sufficient time is provided for spectral estimation. Due to anatomic operation, different regions are associated with flow at different times.

6 Claims, 4 Drawing Sheets (56) References Cited

U.S. PATENT DOCUMENTS

| | | | |
|---|---|---|---|
| 6,104,670 A * | 8/2000 | Hossack et al. | 367/7 |
| 6,673,017 B1 * | 1/2004 | Jackson | 600/437 |
| 2002/0151794 A1 * | 10/2002 | Li | 600/454 |
| 2002/0186868 A1 * | 12/2002 | Bjaerum et al. | 382/128 |
| 2003/0055336 A1 * | 3/2003 | Buck et al. | 600/453 |
| 2004/0193050 A1 | 9/2004 | Ogawa | |
| 2004/0215077 A1 * | 10/2004 | Witt et al. | 600/443 |
| 2005/0137479 A1 | 6/2005 | Haider | |
| 2005/0228276 A1 | 10/2005 | He et al. | |
| 2006/0098853 A1 * | 5/2006 | Roundhill et al. | 382/128 |
| 2007/0078344 A1 * | 4/2007 | Rafter | 600/450 |
| 2009/0082672 A1 | 3/2009 | Guracar et al. | |
| 2010/0022884 A1 | 1/2010 | Ustuner et al. | |
| 2010/0191115 A1 | 7/2010 | Denk | |
| 2011/0208056 A1 * | 8/2011 | Datta et al. | 600/441 |
| 2011/0301466 A1 * | 12/2011 | Wang et al. | 600/454 |

OTHER PUBLICATIONS

Thomas et al., Peak Mitral Inflow Velocity Predicts Mitral Regurgitation Severity, J Am Coll Cardiol 1998; 31:174-9.*

Quinones et al., Recommendations for Quantification of Doppler Echocardiography: A Report From the Doppler Quantification Task Force of the Nomenclature and Standards Committee of the American Society of Echocardiography, J Am Soc Echocariogr 2002; 15:167-84.*

U.S. Appl. No. 12/712,593, filed Feb. 25, 2010.

INPI Search Report and written opinion in counterpart FR application No. 12 00446, filed Feb. 16, 2012, dated Feb. 26, 2013, 16 pages (with translation).

Translation of Office Action from German counterpart application No. 10 2012 101 395 filed Feb. 21, 2012. Office Action dated Jun. 24, 2014, pp. 10.

* cited by examiner

MULTIPLE BEAM SPECTRAL DOPPLER IN MEDICAL DIAGNOSTIC ULTRASOUND IMAGING

BACKGROUND

The present invention relates to spectral Doppler ultrasound. Spectral Doppler ultrasound imaging provides an image of velocities (vertical axis) values modulated by energy as a function of time (horizontal axis). This spectrum may be used for studying fluid flow or tissue motion within a patient. By transmitting a plurality of pulses at a single gate location, a spectral Doppler response is generated in response to received echo signals. The frequency spectrum of the object's motion or flow for a single spatial region is estimated and displayed as a function of time. Flow or tissue deformation parameters can be derived from the acquisition.

Sonographers manually adjust the gate location, gate size, transmit frequency and other spectral Doppler imaging control parameters in order to acquire a desirable image. The gate placement is assisted by display of a 2D B-mode image of the anatomy of interest. Some processes have been proposed for automatic placement of the spectral Doppler gate.

Spectral Doppler ultrasound imaging provides frequency information for a location, so may not provide spatial information. Spectral information may be provided for different depths along a same scan line. Spectral information for other locations or scan lines is acquired sequentially. In a routine scan, the user often places a series of single-gates to optimize the spectrum, and the process is repeated for each location in the same image plane (e.g. mitral valve and mitral annulus). Certain cardiac measurements require evaluating the ratios of peak flow velocity and tissue displacement. In the case of vascular application, multiple gates are placed pre- and post-stenosis to perform clinically relevant assessment. In other scenarios, distinct regions of interest on cardiac walls may need to be studied in relation to each other to evaluate desynchrony in a heart ventricle.

Spatial flow may be represented by color or flow Doppler imaging. The mean Doppler frequency shift or mean velocity for each of a plurality of spatial locations along multiple scan lines is acquired. The mean velocities are mapped to colors. However, mean velocity, such as derived from the change in frequency for Doppler processing, may not provide sufficient information regarding motion.

BRIEF SUMMARY

By way of introduction, the preferred embodiments described below include methods, systems, computer readable media, and instructions for acquiring spatially distinct spectral Doppler information. To acquire spectra data at diverse locations, spatially distinct transmit beams are formed at a same time or during a same transmit event. The transmit beams have laterally spaced foci or peak regions spaced apart from each other. One or more receive beams are formed in response to each transmit beam, providing samples for a plurality of laterally spaced locations. A spectrum is determined for each of a plurality of spatial locations.

In other or additional approaches, samples are acquired for different regions at different times. The scanning for each region is interleaved based on anatomic operation, such as a learned motion pattern determined by a processor. Since spectral estimation relies on a time-continuous series of transmission and reception, the scanning for a region occurs over a sufficient period for spectral estimation before the scanning for a different region occurs. By using anatomic operation, sufficient time is provided for spectral estimation. Due to anatomic operation, different regions are associated with flow or motion at different times. The scanning is controlled to scan the region of flow or motion at the appropriate time based on the anatomic operation.

Split beam or interleaving control may be used independently of each other. In other embodiments, the interleaving control is used with split beam such that spatially distinct transmit beams are transmitted simultaneously for scanning at least one of the regions and may or may not be used for later scanning another of the regions.

In a first aspect, a method is provided for spatially distinct spectral Doppler information. First and second beams are transmitting simultaneously and repetitively from a transducer array along spatially distinct first and second transmit scan lines, respectively. Signals are received repetitively in response to the transmitting from first and second laterally distinct receive locations. The first and second receive locations are within the first and second beams, respectively. First and second spectra are estimated for the first and second receive locations, respectively, from the signals. An image is displayed. The image is a function of at least the first spectrum.

In a second aspect, a non-transitory computer readable storage medium has stored therein data representing instructions executable by a programmed processor for acquiring spatially distinct spectral Doppler information. The storage medium includes instructions for transmitting beams to spaced apart regions, receiving signals for a plurality of laterally spaced locations in response to each of the beams, performing spectral analysis of the signals separately for each of the laterally spaced locations, interleaving the transmitting to the spaced apart regions such that the receiving and performing occurs in a time-continuous manner, and controlling the interleaving as a function of anatomic operation at the spaced apart regions.

In a third aspect, a system is provided for acquiring spatially distinct spectral Doppler information. A transmit beamformer is operable to transmit split transmit beams at a substantially same time. A receive beamformer is operable to form a plurality of laterally spaced receive beams in response to each of the transmit beams, each of the receive beams sampled at a plurality of depths. A processor is operable to estimate a spectrum for each of the depths of each of the receive beams.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Multiple spectral Doppler gates are acquired, automatically and optimized, for accurate analysis of flow through a heart chamber, vessel or any other anatomy of interest. The same approaches are also applicable for analysis of tissue motion. Multiple pulsed wave (PW) acquisitions are used to extract a desired or best spectrum or simultaneously measure flow or tissue motion for two spatially or spatially and temporally distinct regions of anatomy. The acquisition workflow may be improved, providing tools for clinical diagnosis.

Split-beam and/or time-multiplexing of beam groups are used to acquire and process multiple simultaneous spectral Doppler gates. For any given location, time-continuous multiple beams are used to acquire PW samples sufficient to estimate one or more spectra. Spectral Doppler (i.e., Pulsed Wave Spectral Doppler) uses the acquisition of echo signals in a repetitive, continuous manner as compared to Color Doppler were echoes are processed in groups. Spectral Doppler, thus, delivers continuous velocity signals over a longer period. Spectral Doppler provides more accurate flow analysis including: acceleration, spectral broadening, and more reliable detection of aliasing.

The requirement of time-continuous acquisition typically limits the region of interest to a single resolution cell (Doppler gate). Multiple gates can be located along an ultrasound beam (multiple range gates). Parallel receive beamforming allows multiple gates in a lateral direction within the area covered by a transmit beam. Using split beam (parallel transmit beams), anatomical operation-based temporal interleaving, or combinations thereof, two or more spatially distinct (non-neighboring) regions can be interrogated. Spectra for spaced apart regions or a broader region may be obtained as compared to transmitting broad beams to one region alone.

The spectral data may be used to find a desired spectrum, angle correct velocities, identify a jet or flow region (e.g., identify multiple locations associated with a jet or flow), find orientation, and/or analyze tissue motion. Spatial diversity of the spectra may be used to provide more information to the user than a spectrum for one range gate and/or color flow (mean velocity) imaging. The spectra may distinguish between types of flow, such as venous and arterial, where mean velocity may not. Velocity distribution, variation, and intensity information may be determined for multiple locations, providing more motion information. Using split beam or temporal interleaving based on anatomic operation may allow gathering of more or diagnostically relevant spectral information.

Figure 1:
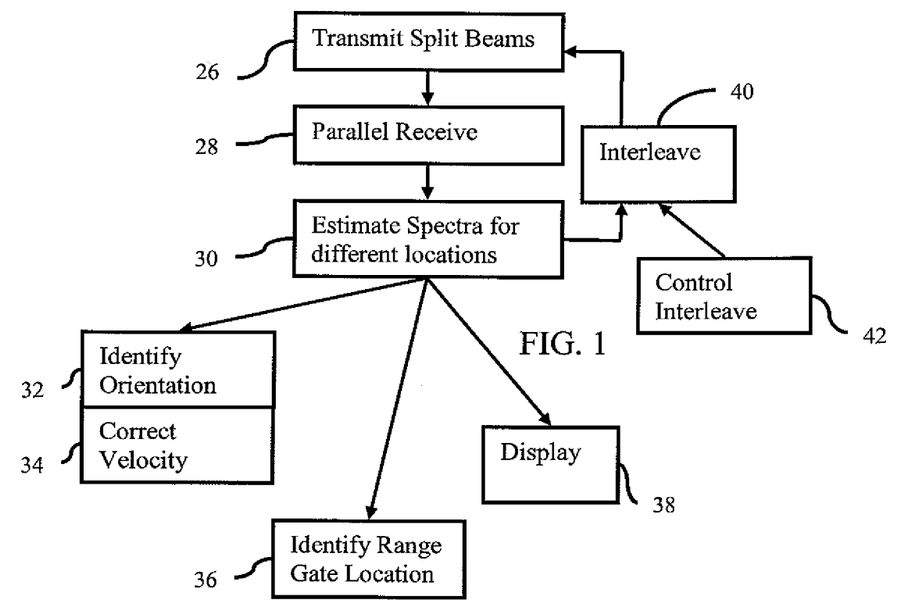
FIG. 1 is a flow chart diagram of one embodiment of a method for acquiring spatially distinct spectral Doppler information.

FIG. 1 shows method for acquiring spatially distinct spectral Doppler information. The method is implemented on the system 10 of FIG. 8 or a different system. The acts are performed in the order shown, but other orders are possible. Additional, different, or fewer acts may be provided. For example, act 26 is replaced with transmission of one transmit beam. As another example, acts 40 and 42 are not performed, using split beam transmission in act 26 without interleaving. Acts 32-38 represent example uses of the spectra obtained using acts 26-30 and/or 40-42. These examples may not be used or other operations may be provided.

Ultrasound samples or signals are obtained for a plurality of spatially distinct locations. The samples are obtained by transmitting beams in act 26. The transmit beams are simultaneously formed in spaced apart regions. The spaced apart regions are separated by a region which is not covered by either of the transmit beams, but may be covered by other transmit beams. For example, two transmit beams are formed at different steering angles, from different origins on the transducer array, and/or from the transducer at different positions. In the near field, the transmit beams may over lap, but for at least a majority of the depth relative to the region of interest or B-mode scan depth, the transmit beams are spaced apart. The −6 dB or −10 dB down edge of the transmit beams are separated by a region of lesser acoustic power from the transmit beams.

For example, simultaneously transmitted first and second beams are spaced apart along at least a majority of a depth of the first beam by having a region in which a plurality of receive lines are not formed in response to the first and second beams (i.e., there is a multi-receive beam wide middle region over a majority of the depth for which samples are not obtained in response to a given split beam transmission). If the receive beams are regularly spaced, receive beams are not formed for a plurality of receive scan lines between the first and second beams.

Other spacing may be provided, such as no overlap of transmit beam profiles or overlap in the far field but not the near field. In an alternative embodiment, the beams overlap along a majority of the depth or more, but different laterally spaced foci are provided. Other separations providing for two or more beams, even with overlap, may be used. The transmit beams are formed along different scan lines.

Two or more beams are transmitted substantially simultaneously, even if covering a contiguous region. Substantially accounts for different delays or start of transmissions due to different foci or steering. Substantially provides for two beams to be transmitted within sufficient time of each other that at least a portion of a wavefront of one waveform is generated acoustically before the last of returned echoes for another wavefront are received at the transducer. The wavefronts from both beams may be transmitted by a majority of the elements of the transducer prior to any reception operation. Simultaneous transmission includes generating acoustic waveforms for one beam while also doing so for another beam, such as transmitting a waveform for one beam from one element while also transmitting a waveform for another beam from another element or the one element.

The split beams (e.g., substantially simultaneous transmit beams along different scan lines) are generated using any possible method. For example, different apertures are formed on the transducer array. Each aperture is for transmitting a different one or ones of the transmit beams. The apertures are unique or do not overlap, such as using right and left halves of the array for two different beams. The apertures may be neighboring sections, may be spatially interleaved (e.g., every other element for one aperture and the other elements for another aperture), or may overlap (e.g., one or more elements transmit waveforms for both beams). The different apertures produce spatially distinct transmit beams by application of a suitable delay and/or phasing pattern.

In another embodiment, one beam is transmitted as a primary beam. The delay pattern, steering angle, apodization, F# or other beam characteristic is set to generate one or more grating lobes. The aperture function is sampled in a way that a grating lobe is produced. The grating lobe or lobes provide one or more other beams. The grating lobes of one beam are used as other transmit beams. Since the grating lobe or lobes are at a different angle from the primary beam, the transmit beams are spatially distinct.

In yet another embodiment, the waveforms for two or more beams are applied to the same or overlapping apertures at a substantially simultaneous time. For each element, the electrical waveforms for the different beams are combined (e.g., summed) based on the separate delay and/or phasing and apodization profiles. The combined waveforms are transmitted from the elements of the aperture, forming the transmit beams substantially simultaneously.

For receive isolation or to limit contribution to received samples for one beam from another beam, different center frequencies, coding, or center frequencies and coding may be used for each beam. For example, frequency multiplexing is used. Two or more transmit pulses having different center frequencies are transmitted. Different delay profiles are used for the pulses at different frequencies so that two or more beams are created in parallel (temporally). For coding, any coding may be used, such as spread spectrum codes or orthogonal codes. Frequency-based codes, amplitude-based codes, phase-based codes, or combinations thereof may be used. In alternative embodiments, no coding or frequency difference is provided. The spatial differences in the transmit beams differentiate the receive signals.

In other embodiments, combinations of techniques for generating substantially simultaneous transmit beams may be used. For example, the aperture is split into two spatially overlapping groups. The groups transmit pulses having different center frequencies so that spatially distinct beams are generated that are separated in frequency.

In addition or as an alternative to split beams (substantially simultaneous or parallel transmit beams), temporally interleaved beams to different regions may be transmitted. For temporally different transmit beams, the spacing may be similar, greater or lesser between the beams as compared to split beams. The transmit beams are separated in time, but are formed for different regions. The different regions may overlap or may be spaced from each other, such as being associated with different parts of the anatomy.

The temporal interleaving is on a scale or period for spectral analysis. In order to obtain samples for spectral analysis, the transmissions occur repetitively. The transmit beams are formed with any pulse repetition interval. By transmitting one or more beams from a transducer array, receiving responsive echoes, and then repeating, a series of samples are obtained for one or more locations. The series includes sufficient samples (e.g., 5 or more) for spectral analysis. The interleaving allows an ongoing series to be acquired, such as over 0.25 seconds or half a heart beat, for a given region. The transmit beam(s) are then formed for another region. The interleaving does not jump between regions prior to acquiring sufficient samples for spectral analysis.

For either the split beam or temporally separated transmit beams, the transmissions are repeated. The repetition allows reception of sufficient samples to perform spectral analysis.

In act 28, signals for a plurality of laterally spaced locations are received in response to each of the transmit beams. Receive beams are formed along a plurality of scan lines in response to each of the simultaneous or temporally interleaved beams. A plurality of scan lines and ranges along the scan lines may be sampled in response to the single transmission. Parallel receive beamforming is provided. The ultrasound samples are obtained at a substantially same time along a plurality of receive beams responsive to a same transmit beam. In alternative embodiments, sequential receive beamforming or a combination of parallel and sequential receive beamforming is used. Other plane wave transmission and reception techniques may be used, such as applying a Fourier transform to electrical signals at each element to generate an array of values representing response at different locations.

Figure 3:
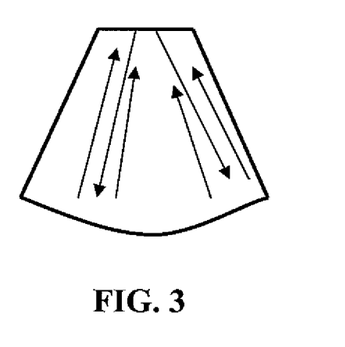
FIG. 3 is a graphical representation of parallel beamforming in a region of interest.

FIG. 3 shows one embodiment where one transmission of split beams in act 26 is used to acquire a plurality of receive beams in act 28. While two receive beams are shown, a greater density may be provided, such as four, eight, sixteen, thirty two, sixty-four, or other number of receive beams per transmit beam. The transmit and receive beams intersect a region of interest. The region of interest may be any size or shape. The region of interest defines the spatial locations for which spectra are estimated in response to a given transmit event. For example, at least one hundred spectra for respective spatially different spatial locations within the region of interest are calculated. Multiple regions may be scanned.

The receive operation occurs repetitively in response to the transmitting. Signals from laterally distinct receive locations within the transmit beams are received. By forming a plurality of receive beams in response to each of the transmit beams, signals for many receive locations are obtained substantially simultaneously. Samples for the same locations are acquired over time. Ultrasound samples are obtained over a period, such as acquiring five or more ultrasound samples for each spatial location. Any scan sequence and/or pulse repetition frequency may be used. For other regions, the reception of act 28 in response to different transmit beams is repeated to acquire samples for the other regions.

In act 30, spectra are estimated for the receive locations. A spectrum is estimated for each of the spatially distinct locations. The spectra are estimated from the ultrasound samples from different depths and/or lateral locations. The spectra correspond to a period in which the samples were acquired. For each spatial location of interest, such as all the locations in a region of interest, in an image field, or other distributions, a spectrum is calculated. Spectra may be determined for only a subset of the spatial locations, such as determining the spectra for sparsely sampled locations or densely sampled locations but in a limited region.

Figure 4:
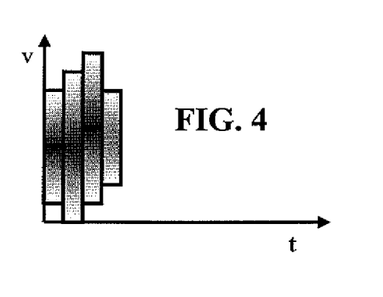
FIG. 4 is a graphical representation of a spectral strip display.

For each receive location, a spectrum or series of spectra are estimated from the received signals. FIG. 4 shows a spectral strip of spectra for a same location over time. Different spectra may be estimated for the same spatial location at different times corresponding to different periods of acquisition.

The spectral analysis of the signals is performed separately for each of the laterally spaced locations on respective scan lines. The signals for each given location are used for spectral analysis without signals from other locations. In alternative embodiments, the signals are spatially and/or temporally filtered prior to spectral analysis, but separate spectra are provided for each location.

A set of spectra for a given time or representing the sampling period are estimated. For parallel receive beamforming, the spectra may represent the same period. In one embodiment, all of the spatial locations for determining spectra are sampled at a same time (e.g., same transmit and receive events). In other embodiments, sequential acquisition is used. The spectra are sampled at a same time relative to a physiological cycle, such as the heart cycle. Spectra for only one period may be estimated. Alternatively, spectra for the same locations are estimated for different periods to provide time varying spectral information. The samples used for estimating the spectra at a given time may be used for estimation at another time as well, such as associated with repeating estimations using a temporally moving window for selecting the samples.

The spectra are estimated by applying a Fourier transform, wavelet transform or Wigner-Ville distribution to the ultrasound samples representing each of the spatially distinct locations. Spatially distinct locations correspond to different range gates, such as different center positions, sizes or both, with or without overlap. Any transform may be applied to determine the spectrum for each of the spatially distinct locations. The spectra represent energy as a function of frequency (See FIG. 2).

The spectra from spatially distinct locations may be used for various purposes, such as to determine a range gate location for a spectral Doppler display, calculate a parameter (e.g., volume flow, maximum flow velocity, size or shape of a flow region, ratio of flow volumes, or ratio of volume flow, such as a ratio for comparison of flow at a bifurcation), determine orientation, find flow location, distinguish tissue motion and flow, angle correct velocities, set a velocity scale, or analyze tissue motion. By providing spectra from different spatial locations, more information may be provided to a user than by using color Doppler (mean) velocity, variance, or energy imaging or than by using spectral Doppler for a given range gate. Any characteristic of the spectra may be used, such as the maximum velocity, minimum velocity, mean velocity, median velocity, energy and velocity information, maximum energy, velocity associated with maximum energy, variance of velocity, slope or trend in the spectra, or location of change of slope. Instead of the mean velocity or energy of the mean velocity, other information may be provided. Different types of spectral information may be useful for different diagnostic purposes. For example, the maximum velocity may more accurately indicate tissue health. The variance of the spectra may indicate flow conditions. The useful information provided in spectral strips is available for many locations at a same time, providing spatial distribution information. Locating the spectrum with the maximum velocity may provide better flow information than a user guessed position. Using split beam or temporal interleaving based on anatomy, spectral information is provided for the anatomical regions of interest.

Any now known or later developed techniques may be used to characterize or determine a characteristic of the spectra. For example, the highest velocities above a threshold level with only one or no lower velocities below the threshold indicate the maximum velocity. The maximum velocity is the highest or an average of the two or more highest velocities associated with contiguous values above the threshold or noise level in the spectrum.

In one embodiment represented in act 32, an orientation of a flow or tissue motion region is identified from the spectra. A criterion is applied to the spectra from the different locations. For example, the maximum velocity is identified for each spectrum. If the maximum velocity is above a threshold or within a range of values, the location is associated with tissue motion or flow. By examining the spectra of the various locations, the line, area, or volume associated with motion or flow is identified. The spatial distribution may be filtered, such as low pass filtering.

Line, model, shape, template or other fitting is applied to the identified region. Templates for different types of flow or motion may be used. For example, a cone, cylinder, ellipse, or other shape is fit to the locations of flow or motion. The center length axis or other axis of the fit shape indicates orientation. Region growing, skeletonization, or other processes may be used to find a primary axis or direction of flow. Alternatively, more than one orientation of flow or motion is identified, such as associated with turbulence or bifurcation.

The spatial distribution of flow may alternatively or additionally be used for calculating an area or a volume, such as a volume of a jet. Other parameters may be determined, such as finding a smallest cross section of a volume with the cross section being through a location with the maximum velocity. The cross-section is used as an area, such as orifice area, for calculating volume flow. Templates for different conditions may be matched to the spatial distribution, such as by scaling and determining a template with a greatest correlation. A condition is identified from the template with the greatest correlation.

In act 34, the velocity is corrected as a function of the orientation. Ultrasound velocities are estimates of the velocity towards and away from the transducer or along the scan line. The orientation may be used to adjust or correct the velocity to represent actual velocity along the direction of travel. Due to turbulence, the orientation may be different for different regions. One orientation may be used or multiple orientations depending on the location and time may be determined. For example, a flow map representing velocity vectors as a function of time is determined Local orientations are identified and used for angle correction.

The spectral velocities and/or color Doppler velocities may be corrected. The velocity is divided by the cosine of the angle between the scan line and the orientation (i.e., angle between the sound propagation direction and the flow vector).

In one example, velocity correction is performed for flow through a vessel. By measuring flow at different positions along a vessel and by matching the flow with morphological information (e.g., matching to a vessel flow template), the orientation of a vessel is determined. The accuracy of volume flow measurements can be improved by angle correcting the velocities through the vessel.

In the example use of act 36, a location for a range gate is identified as a function of the spectra. The identification of a range gate location is for display of the range gate and/or associated spectra. The spectral estimation for other locations may continue or not after identifying the range gate location. As all sampled locations may be considered range gate locations, the location associated with maximum flow or other characteristic is identified as the range gate of interest.

Figure 6:
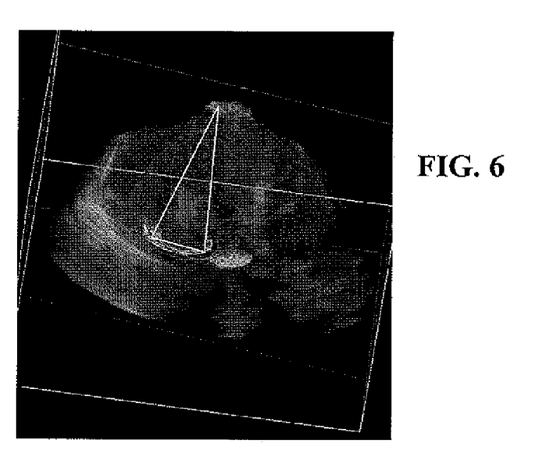
FIG. 6 is an ultrasound image showing motion information in one region determined from spatially distinct spectra.
Figure 7:
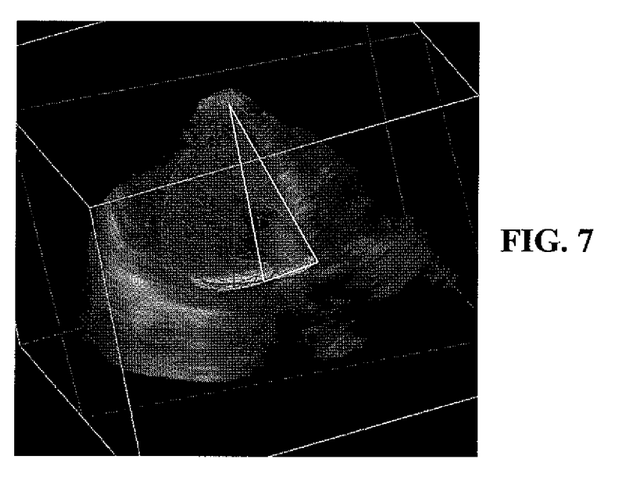
FIG. 7 is an ultrasound image showing motion information in another region determined from spatially distinct spectra.

Other uses of the spatially distributed spectral information are possible. The spectral information can further be used to differentiate between tissue and blood flow based on velocity and/or signal intensity. Tissue velocities, flow velocities, and morphological information may be co-registered. The spectral information indicates tissue and flow locations. The spatial distribution of tissue and flow information may indicate a type of anatomy or morphology. FIGS. 6 and 7 show scans with flow and moving tissue regions highlighted differently.

Having spectral Doppler data available for larger regions and for spatially distinct regions may allow comparison of flow or motion at different locations. Where split beam is used, the different locations may be spaced apart, such as at different lateral edges of a region scannable by a given transducer. Rather than accept errors associated with manual placement, automated gate placement at optimized locations allows for better comparison between spatially diverse regions. Since split beam may be used, the comparison is for the same time, reducing errors due to temporal acquisition.

Spatial distribution of spectral analysis may allow for accurate volume flow calculation. An area of flow, such as at an orifice, is determined. Using the spectra, the flow at each location in the area may be determined. The volume flow through the orifice or other locations is calculated using the spectral information for position and/or flow.

In act 38, an image is displayed. The image is a function of at least one of the spectra for the plurality of spatially distinct locations. The spectra are used to provide information to the user in a representation of a region, as a numerical quantity, or through graphics displayed as the image. Any function may be used, such as mapping, modulating, selecting, or comparing. The image may provide information associated with only one spectrum, but be a function of spectra from different spatial locations. For example, the spectra are compared to select one of the spectra for display or to display a difference.

Any technique may be used to provide the spatial information to the user. In one embodiment, a spectral strip is used. Multiple strips may be used, where each strip represents the spectrum over time for a different spatial location. Only one strip may be used, but still be a function of spectra from different spatial locations. For example, one of the spectra is identified as a function of a spectral characteristic. The values of the same characteristic of the spectra are compared. One is selected, such as identifying the spectrum having a maximum frequency. The average of the characteristic over time may be used for the selection. The selection may be constant after identification. Alternatively, the selection varies as a function of time. The selection through comparison is performed periodically, every time increment of the spectral strip display, or in response to a triggering event. In other embodiments, spectra from different spatial locations are combined, such as averaging the frequency bins of a plurality of spectra from different spatial locations.

A spectral strip representing the selected spectrum or otherwise combined spectra is displayed. FIG. 4 shows an example spectral strip display simplified for illustration. The spectral strip shows the frequency modulated by energy as a function of time. Any now known or later developed spectral strip mapping may be used, such as gray scale mapping with the intensity representing energy. Filtering may be applied to smooth the spectrum. Characteristics of the spectral strip may be determined and displayed, such as graphically tracking a maximum velocity as a function of time in the spectral strip.

In another embodiment, a representation of a difference between spectra at different locations is displayed. The difference in flow between two spatially (or temporally) distinct acquisitions may quantitatively show flow changes over distance or time. The difference may be shown by color coding the spectra differently and overlaying or compounding them. Alternatively, a difference in amplitude at each frequency is calculated and displayed. Any difference may be used. Spectral data from a previous examination may be acquired and compared with a current spectrum. The difference may be displayed to show changes over time, such as sixth months, or between locations, such as between locations from different beams of a split beam.

In one embodiment, the spectral strip is displayed with a spatial image, such as a one-dimensional M-mode, two-dimensional B-mode, two-dimensional color flow mode, or combination thereof image. The location of the selected spectrum or spectra may be indicated graphically in the image. For example, text, color, symbol, or other indicator shows the user the location for the automatically determined range gate corresponding to the selected spectrum. The user may add other range gate spectral displays for comparison. Where multiple spectra are displayed, matched color coding between the acquisition range gates and displayed spectra may be used. For example, the indication of the location of the range gate uses orange. The corresponding spectrum is shaded in orange, outlined in orange, or otherwise labeled in orange. Other indications may be used, such as text labels or numbering.

A spatial image may be generated, such as shown in FIGS. 6 and 7. The image is a one, two, or three-dimensional representation. A one, two, or three-dimensional region representing the spatially distinct locations is displayed. For example, an M-mode image is generated. The image represents information from spatial locations along a line or curve, shown as a function of time. As another example, a two-dimensional image of a plane is provided. In another example, a three-dimensional representation is rendered from data representing a volume.

The represented region is along a scan axis, such as azimuth, elevation, and/or range, or is along different axes. For example, an arbitrary plane is defined through a volume. Spectra from spatial locations on or near the arbitrary plane are used for generating the spatial image. In other embodiments, the plane or line is positioned along a scan axis.

A display value for each of the spatial locations in the image is a function of a respective spectrum. The pixels may be modulated or mapped as a function of a characteristic of each spectrum, representing spectral information at each distinct spatial location. For example, the maximum velocity is determined for each spatial location within a region of interest. Full or sparse sampling may be used. Other Doppler frequency shift or spectral characteristics may be used. Since different spectra occur at different locations due to different tissue movement or flow, the spatial image displays the variance in spectra as a function of space. Due to filtering or combining of spectra, the spectrum for a distinct spatial location may be a function of multiple spectra.

In one embodiment, the spectra are used to classify a type of flow or motion, and the mapping function or other display value characteristic is selected based on the classification. For example, the spectra may distinguish between arterial and venous flow for each of the spatially distinct locations. Arterial flow may have greater velocity or frequency variation, higher maximum velocity, or other characteristics at a given time for arterial flow. The variance as a function of time may distinguish an arterial flow location from a venous flow location.

Any characteristic of the image may vary as a function of the spectral information. For example, the grey scale level, the color, the hue, the brightness, or other characteristic varies with variation in the spectra characteristic. In the arterial verses venous flow example above, arterial and venous flow may be represented by different colors, such as B-mode, mean velocity, or other values assigned a base color of red or blue depending on being an arterial or venous flow location (i.e., similar to color flow mapping for velocity to and away from the transducer). The brightness or shade of each color is a function of different information, such as the maximum or mean velocity. As another example, the display value is modulated or varies as a function of the maximum velocity derived from each spectrum. The other characteristics of a given pixel may be a function of information from the spectra or different information.

The image may be displayed as a function of time. The one, two, or three-dimensional image varies as a function of time. The image is re-generated with more recently acquired spectral or other information. For example, a moving window defines the most recently acquired data set, such as the most recent 5-10 samples with the window shifting by 1, 2, or other number of samples, for calculating the spectra. The most recent spectral information is used to generate the image of the region. The image changes as the spectra and/or other information change.

Other images may be displayed. For example, a B-mode image, color flow image, or combined B-mode and color flow image are displayed adjacent to but separate from a spectral strip image or other image based, at least in part, on spectral information from different spatial locations. Separate images on a same display at a same time may be used with or without overlap. Alternatively, an image generated from spectral analysis information is overlaid on a B-mode or other image. For example, FIGS. 6 and 7 show B-mode images with different locations highlighted differently depending on the type of motion. The type of motion is determined from the spectral information.

Using the split beam or temporal interleaving, the transmitting of act 26, the receiving of act 28, and the estimating of act 30 are performed for a particular region or regions. The region or regions are part of a total region to be analyzed or are the entire region to be analyzed. The acts may be repeated for the region or regions. The repetition occurs in a time-continuous manner such that other transmissions and receptions for estimating spectra for another region do not intervene.

By using a wide beam or receiving along multiple receive scan lines in response to a give transmission, spectra are acquired for a region with multiple lateral locations. Using split beam, spectra may be acquired for a larger region or for regions spaced apart. For example, two overlapping or completely separated regions are scanned with split beam. Flow phenomena may be automatically observed in multiple locations. Where the flow or motion is to be monitored at a same time, the split beam allows spectral analysis for different or separated locations. Correlations or the most appropriate beam configuration for a given measurement may be set for the different regions. Diagnosis may be assisted by having information from regions accessible by a transducer at a same location and same time only by having transmit beams formed over different regions.

Additionally or alternatively, anatomical information may be used for acquiring spectral information from different regions at different times. The acts may be repeated with temporal interleaving, such as where spectra are estimated for one region during one period, estimated for a different region during another period, and then return to the one region for repeated temporal interleaving.

In act 40, the transmitting, receiving, and estimating are repeated for a different region or regions. The interleaving is between two or more sets of regions. Split beam or wide beam scanning is performed for each of the regions. Spectra for different lateral and/or depth locations are acquired during a given period of scanning a region before switching to another region. By temporally interleaving spatially distributed spectra estimation, information for different anatomical regions may be acquired automatically for comparison and/or diagnosis. For example, a small 3D volume shows a spatial/temporal anomaly, such as a jet. A temporal/spatial analysis may confirm or rule out aliasing. The split beam approach may keep one beam at the location of the anomaly and move the other transmit beam around to confirm or rule out the presence of a jet.

Figure 5:
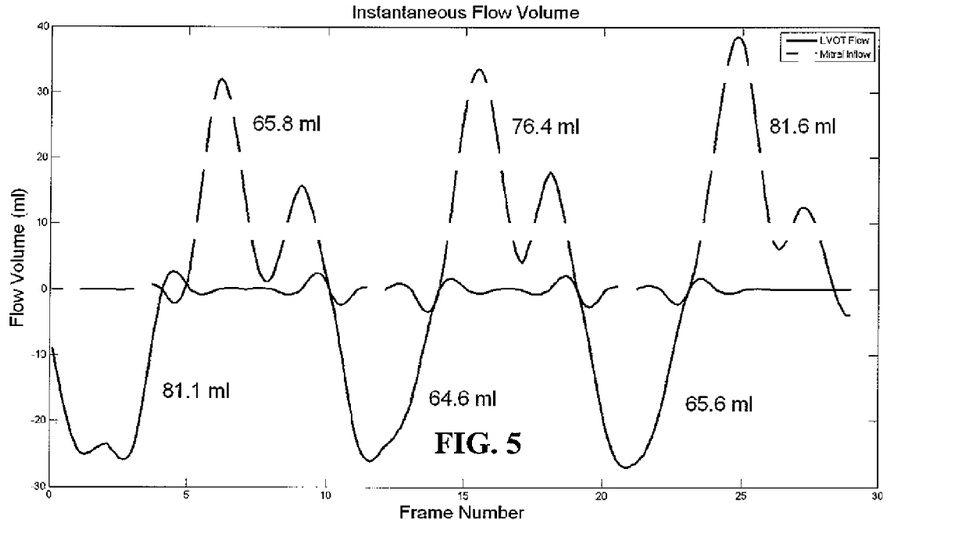
FIG. 5 is a graphical representation of flow volume for two different regions.

In one embodiment represented in FIG. 5, temporal interleaving is performed as a function of a physiological cycle. Volume scans for spectral estimation are performed for the left ventricle outflow track and the mitral valve. The volume scans cover the regions of likely jetting of the fluid flow and/or movement of the valves or associated tissue. The spatial and temporal location of the beam or beams may be provided by an algorithm that uses motion pattern recognition from previously acquired data or image sequence. The type of measurement requested by the user may result in a given spatial and/or temporal beam pattern. Machine learning algorithms may model flow or motion based on a ground truth position for beam location and spectral analysis. Using current data, the spatial and temporal beam position and spectral analysis (gate locations) may be selected using the model.

In the example of FIG. 5, the temporal interleaving is a function of a physiological cycle, such as the heart cycle. The estimating of spectra for each of the two regions is performed at different times. Since each anatomical region operates at different times, the temporal interleaving is controlled in act 42 based on the cycle. Transmissions and associated estimation occur for one region while not occurring for the other region during one portion of the heart cycle. For another portion of the heart cycle, the transmissions and associated estimation occur for the other region while not occurring for the original region. For example, the flow volume for the mitral valve is near zero for about half the heart cycle and larger for the other half. The flow volume for the left ventricle outflow tract has an opposite LVOT temporal pattern.

In FIG. 5, about three to fifty volume frames are acquired for every half heart cycle. Each frame represents acquisition of one sample at each spectral location. For frames 1-4, 10-14, and 19-23, the scanning and estimation occur for the LVOT flow. For frames 5-9, 15-18, and 24-28, the scanning and estimation occur for the mitral valve. The interleaving automatically switches between the two regions based on the heart cycle. Spectra are estimated for each region during the time of greatest flow. The volume flow for the regions is determined and may be compared. While flow is less in one region, the other region is scanned and vice-versa.

During the scanning of a given region, the scanning occurs in a time-continuous manner for pulsed wave Doppler. Sufficient samples are acquired for estimating at least one spectrum for each of the locations. The time multiplexing is not interleaving acquisitions for multiple beams where each beam is acquired less often. Instead, two or more locations are probed in a manner that is synchronized with physiological processes such as breathing or the heart rate.

The breathing or heart cycle may be derived from ECG or respirometer signals. Alternatively, the spectra or other data (e.g., color Doppler, PW energy, or B-mode) is used to determine the cycle. Motion of tissue or flow pulsation is determined from ultrasound data and represents the cycle.

The interleaving is controlled as a function of anatomic operation at the spaced apart regions. The flows or motions for different anatomy are diagnostically useful at different times due to the operation of the anatomy. By using the anatomy operation, useful spectral information may be obtained as part of a same examination of the patient. Since the anatomy operation is tied to the physiological signal, the interleaving is controlled as a function of a physiological cycle. Alternatively, the regions are sampled and spectral information indicates the frequency or relative times at which anatomy regions of interest are operating. The transmitting is performed for a first portion of the physiological cycle at a first one of the spaced apart regions and performed for a second portion of the physiological cycle at a second one of the spaced apart regions. The portions may be the entire cycle or a sub-set. The cycle itself may be insufficient. Knowledge of the anatomy relative to the cycle is used to determine which region to scan and when within the cycle. As an example, the flow through the mitral valve and the flow through the LVOT, flow through two spatially distinct regions in the heart, are naturally separated in time. Other anatomical locations may share similar separation. In Tissue Doppler Imaging, clinicians may record wall motion at different spatial locations at different times.

The control of the interleaving may account for other factors. For example, the user indicates the parameter to be measured with the spectral analysis. In the example of FIG. 5, volume flow per cycle is measured. In other embodiments, the volume flow in a typically non-flow period is to be measured, such as to determine leakage. In response to user indication of leakage measurement, the interleaving and associated transmissions are adjusted to scan the regions in an opposite manner.

The results of the spectral analysis may be used for other control. The transmitting and interleaving are automatically adjusted as a function of an output of the spectral analysis. The spectra are analyzed, such as identifying the location for maximum velocity or other characteristic. Based on the location, the timing and/or location of the scanning are adjusted. The scan region may be shifted, broadened, narrowed or otherwise changed to better cover the region of interest. An appropriate beam configuration for a given measurement is selected and/or adjusted. The timing for interleaving may be adjusted to position the maximum flow region earlier, in the middle or later in the period for scanning a given region.

Figure 8:
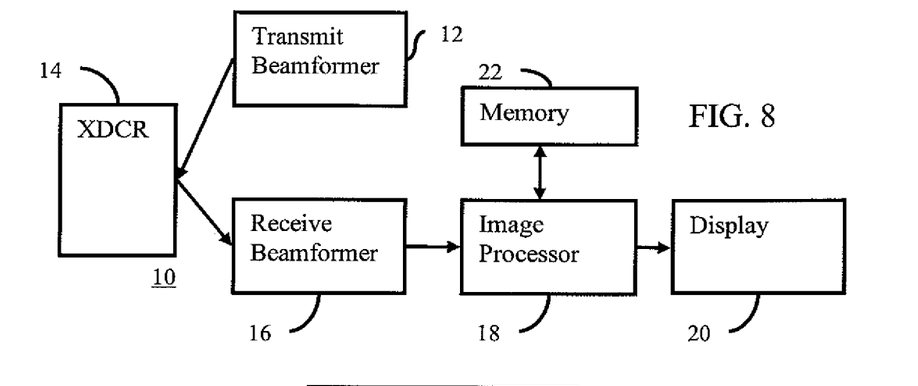
FIG. 8 is a block diagram of one embodiment of a system for acquiring spatially distinct spectral Doppler information.

FIG. 8 shows a system 10 for acquiring spatially distinct spectral Doppler information. The system 10 is a medical diagnostic ultrasound imaging system, but other imaging systems may be used, such as a workstation. The system 10 estimates spectra for different locations substantially simultaneously. Substantially accounts for sequential processing for data sampled in a same scan, such as sequential beamforming, but using the same transmit and receive event.

The system 10 includes a transmit beamformer 12, a transducer 14, a receive beamformer 16, an image processor 18, a display 20, and a memory 22. Additional, different or fewer components may be provided, such as the system 10 without the front-end beamformers 12, 16 and transducer 14 or the system 10 with a scan converter.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, combinations thereof or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit beamformer 12 is shown separately from the receive beamformer 16. Alternatively, the transmit and receive beamformers 12, 16 may be provided with some or all components in common. Operating together or alone, the transmit and receive beamformers 12, 16 form beams of acoustic energy for scanning a one, two, or three-dimensional region. Vector®, sector, linear or other scan formats may be used.

The transmit beamformer 12 is a processor, delay, filter, waveform generator, memory, phase rotator, digital-to-analog converter, amplifier, combinations thereof, or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. In other embodiments, the transmit beamformer 12 includes switching pulsers or waveform memories storing the waveforms to be transmitted. Other transmit beamformers 12 may be used.

The transmit beamformer 12 is configured as a plurality of channels for generating electrical signals of a transmit waveform for each element of a transmit aperture on the transducer 14. The waveforms are unipolar, bipolar, stepped, sinusoidal, or other waveforms of a desired center frequency or frequency band with one, multiple, or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles, coding, and combinations thereof.

The transmit beamformer 12 is operable to transmit one or more transmit beams of ultrasound energy substantially simultaneously. A transmit beam originates from the transducer 14 at a location in the transmit aperture. The transmit beam is formed along a scan line at any desired angle. The acoustic energy is focused at a point along the scan line, but multiple points, line focus, no focus, or other spread may be used. The transmit beam substantially covers a wide region, such as being divergent, a plane wave, collimated, unfocussed, weakly focused, or focused to cover multiple receive lines. Substantially accounts for sufficient acoustic energy to provide echoes and imaging above noise. In one embodiment, the transmit beam is sufficiently wide to cover up to 64 receive beams or scan lines distributed in a column (e.g., 8×8), a plane (1×64), or other arrangements (e.g., 4×16). By controlling the apodization, aperture, and delay profile, different size regions may be scanned with a given transmit beam.

The transmit beamformer 12 may generate split beams. The split beams are formed for pulsed wave spectral Doppler estimation for two regions substantially simultaneously. Split beams may be used for scanning different regions at different times, such as associated with temporal interleaving. In alternative embodiments, such as with temporal interleaving of pulsed wave spectral Doppler estimation for different regions, a single transmit beam is formed for each transmit event.

For split beams, more than one transmit beam is generated substantially simultaneously. For example, a transmit beam is generated with a grating lobe. The focus, apodization, aperture (e.g., discontinuous selection of elements), or other characteristic is set to cause a grating lobe at sufficient amplitude for generating echoes above any noise. A high amplitude transmit beam may be steered at an angle away from normal to the array to generate the grating lobe. Samples are received in response to the primary beam and the grating lobe. As another example, the transducer array is divided into two or more apertures. The separate apertures are used to form the different transmit beams. In another example, frequency or other coding is used. For yet another example, the same aperture is used to transmit multiple beams by combining delayed waveforms for both beams at each element. Combinations of these examples may be provided.

The receive beamformer 16 is a preamplifier, filter, phase rotator, delay, summer, base band filter, processor, buffers, memory, combinations thereof, or other now known or later developed receive beamformer component. Analog or digital receive beamformers capable of receiving one or more beams in response to a transmit event may be used. For example, the receive beamformer 16 has sufficient processing power and/or hardware components to substantially simultaneously form 64 or other number of receive beams in response to a same transmit. Parallel and/or sequential processing may be used to form different beams. Parallel beamforming may be provided without storing ultrasound samples for each element for an entire receive event in a memory. Alternatively, a memory may be used to store the ultrasound samples for each element.

The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay for applying apodization amplification. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. The summer sums the relatively delayed and apodized channel information together to form a beam. In one embodiment, the beamform summer is operable to sum in-phase and quadrature channel data in a complex manner such that phase information is maintained for the formed beam. Alternatively, the beamform summer sums data amplitudes or intensities without maintaining the phase information. Other receive beamformation may be provided, such as with demodulation to an intermediate frequency band and/or analog-to-digital conversion at a different part of the channel.

For parallel receive operations, different delays, apodization, and summing are provided for the different beams. For split beam, equal or different numbers of parallel beamforming are used for each beam. For example, two transmit beams are formed. Thirty two receive beams are formed for each of the two transmit beams. As another example, eight receive beams are formed from one transmit beam and twenty four receive beams are formed from another transmit beam.

Beamforming parameters including a receive aperture (e.g., the number of elements and which elements used for receive processing), the apodization profile, a delay profile, a phase profile, imaging frequency, inverse coding, and combinations thereof are applied to the receive signals for receive beamforming. For example, relative delays and amplitudes or apodization focus the acoustic energy along one or more scan lines. A control processor controls the various beamforming parameters for receive beamformation.

One or more receive beams are generated in response to each transmit beam. For example, up to 64 or other number of receive beams are formed in response to one transmit beam. Each receive beam is laterally spaced in two or three-dimensions from other receive beams, so samples are acquired for different lateral locations.

Acoustic echoes are received by the transducer 14 in response to the transmit beam. The echoes are converted into electrical signals by the transducer 14, and the receive beamformer 16 forms the receive beams from the electrical signals. The receive beams are collinear, parallel and offset or non-parallel with the corresponding transmit beam. The receive beams may be adjusted to account for spatial two-way differences, such as adjusting the delay profile and/or amplitude differently for receive beams closer to the transmit beam center than for receive beams spaced further from the transmit beam center. Alternatively, a single receive beam is generated for each transmit beam.

The receive beamformer 16 outputs data representing different spatial locations of a scanned region. The receive beamformer 16 generates samples at different depths along each receive beam. Using dynamic focusing, samples are formed for different depths. The ultrasound data is coherent (i.e., maintained phase information), but may include incoherent data. Once the channel data is beamformed or otherwise combined to represent spatial locations of the scanned region, the data is converted from the channel domain to the image data domain.

The image processor 18 includes a spectral Doppler processor and/or imaging detectors. A separate control processor is provided as part of the image processor 18. Alternatively, the processor or processors used for estimation or detection control the imaging and/or system 10. The image processor 18 is a general processor, control processor, digital signal processor, application specific integrated circuit, field programmable gate array, analog circuit, digital circuit, combinations thereof or other now known or later developed device for processing.

Figure 2:
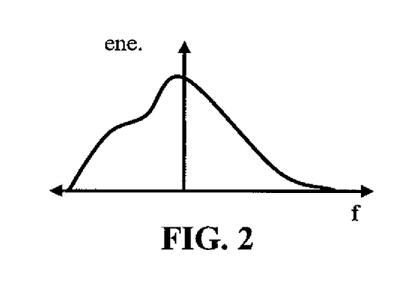
FIG. 2 is a graphical representation of a spectrum.

In one embodiment, the image processor 18 is a digital signal processor or other device for applying a transform to the receive beam data. A sequence of transmit and receive events is performed over a period. A buffer or the memory 22 stores the receive beamformed data from each transmit and receive event. Any pulse repetition interval may be used for the transmit beams. Any number of transmit and receive events may be used for determining a spectrum, such as three or more. The image processor 20 is operable to estimate a spectrum for each of the depths of each of the receive beams. By applying a discrete or fast Fourier transform, or other transform, to the ultrasound samples for the same spatial location, the spectrum representing response from the location is determined. A histogram or data representing the energy level at different frequencies for the period of time to acquire the samples is obtained. FIG. 2 shows one example spectrum for a spatial location.

By repeating the process, the image processor 20 may obtain different spectra for a given location at different times. Overlapping data may be used, such as calculating each spectrum with a moving window of selected ultrasound samples. Alternatively, each ultrasound sample is used for a single period and spectrum.

A spectrum is determined for each of a plurality of spatial locations, such as for over 200 depths on each of 64 or other number of receive beams. The data for each location is transformed. The image processor 18 may include a plurality of components for parallel processing or a single component for parallel or sequential estimation. The scan region may be shifted, such as transmitting and receiving at different locations. Any scan pattern may be used. For example, a volume is scanned. Transmit beams are scanned for one or more regions before being shifted to scan one or more different regions. The scan pattern may provide for complete acquisition of sufficient samples for transform before shifting location.

The image processor 18 may derive information from a given spectrum or from a plurality of spectra. In one embodiment, the image processor 18 determines an orientation, area, or volume of flow from the spectra for the depths and receive beams. By determining a maximum velocity or other characteristic of each spectrum, locations associated with motion or flow may be identified. A threshold or other criteria are applied to distinguish velocities of interest from other velocities. Other calculations, comparisons, selections, or other functions may be performed by the image processor 18 using the spectral information. For example, a location for which a PW spectral Doppler strip is to be displayed is selected.

The image processor 18 may control operation of the spectral analysis. Various functions may be performed in an automated manner. For example, the image processor 18 controls the beamformers 12, 16 to interleave between multiple regions. The regions may be indicated by a user or automatically determined. The image processor 18 controls the interleaving between regions for spectral analysis using anatomical information. The user inputs the type of anatomy (e.g., by selecting an application specific to a type of anatomy), or the image processor 18 determines the type of anatomy by image processing (e.g., processing a B-mode image to identify anatomy).

Based on the type of anatomy, the operation of the anatomy is determined. The operation may be predetermined, such as by programming operation of the system 10 for a given anatomy. Alternatively, the image processor 18 determines flow or motion operation of the anatomy based on the spectra. Using the anatomical operation, the interleaving may be controlled to provide spectral information for different regions of the anatomy at different times.

The image processor 18 may perform automatic velocity scale identification for color Doppler imaging. The spectral velocity estimates on a few sparse spectral firings are acquired. The mean velocity or the maximum velocity is determined from the spectra or a spectrum. The velocity scale is set for color Doppler accordingly.

The image processor 18 generates display values as a function of the spectra. Display values include intensity or other values to be converted for display, values provided to the display 20 (e.g., red, green, blue values), or analog values generated to operate the display 20. The display values may indicate intensity, hue, color, brightness, or other pixel characteristic. For example, the color is assigned as a function of one characteristic of a spectrum and the brightness is a function of another spectrum characteristic or other information. The display values may be combined with other display values, such as blending or overlaying display values determined, at least in part, from spectral information with B-mode information.

The display values are generated as a function of the spatial spectral information in any type of display format. For example, the display values are generated for a spectral strip display. The different spectra are compared. The spectrum with the highest velocity over a noise floor is selected for display. A spectrum for a location with an averaged maximum velocity over time may be selected. The selected spectrum is used for the spectral display. The spectra for the same location are used over time. Alternatively, the spectrum with the highest velocity is used for each time increment of the spectral strip regardless of location. Multiple spectral strips may be displayed for visual comparison.

In another embodiment, a one, two, or three-dimensional representation is generated. For example, display values are generated for a two-dimensional image representing a region sampled by the receive beams. A display value is provided for each pixel and/or sample location. The display values for each location of the two-dimensional image are a function of the respective spectrum. For example, the maximum velocity is identified in each spectrum. The display values are modulated by the maximum velocities, such as mapping color and/or brightness based on the maximum velocity. Any mapping may be used, such as color mapping used for color flow.

The image processor 18 may include a B-mode detector for determining intensity and/or a color Doppler detector for determining average velocity, variance, and/or energy. One or more filters, such as clutter, spatial or temporal filters may be provided. The detector outputs incoherent image data. Additional processes, such as filtering, interpolation, and/or scan conversion, may be provided by the image processor 18.

A spatial image may be generated as a function of both spectra and mean velocity. The difference between color Doppler (qualitative) and spectral Doppler (quantitative) methods is blurred or blended. The number of firings at a given scan-angle is increased to get the spectrum (quantitative). The number of firings to get color Doppler (qualitative) is decreased. A sparse-sampled spectral Doppler firing scheme is combined with a finer-sampled color Doppler acquisition scheme (e.g. assume 16 firing angles where 4 are used for spectral Doppler estimation and the rest are used for color Doppler estimation). A quantitative color Doppler image is provided by combining the spectral velocity information and the color-Doppler velocity information with interpolation. A moving average of the color-samples indicates quantitative color Doppler.

The display 18 is a CRT, monitor, LCD, plasma screen, projector or other now known or later developed display for displaying an image responsive to the display value. For a black and white spectral Doppler image, a range of velocities with each velocity modulated as a function of energy is provided as a function of time. The selected spectrum indicates the velocity and energy information for a given time. The intensity of a given pixel or pixel region represents energy where velocity is provided on the vertical scale and time provided on the horizontal scale. Other image configurations may be provided, including colorized spectral Doppler images. For spatial imaging, an M-mode type image of maximum velocity or other characteristic determined from the spectra along a line is provided. The brightness along a line is mapped as a function of time. A two-dimensional image may be generated from the display values. Display data representing a volume may be rendered using any three-dimensional imaging.

The memory 22 stores buffered data, such as ultrasound samples for spectrum estimation. The memory 22 may store display values or images, such as a CINE memory. In one embodiment, the memory 22 is a non-transitory computer readable storage medium having stored therein data representing instructions executable by the programmed processor 18 for acquiring spatially distinct Spectral Doppler information. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. In a non-transitory computer readable storage medium having stored therein data representing instructions executable by a programmed processor for acquiring spatially distinct Spectral Doppler information, the storage medium comprising instructions for:
   transmitting a sequence of first beams to a first region spaced apart from a second region, the sequence of the first beams being transmitted during a first period of time;
   transmitting a sequence of second beams to the second region during a second period of time different from the first period;
   repeating the transmitting of the sequences of the first and second beams;
   controlling the repeating so that the transmissions to the first region are at different times than the transmissions to the second region based on a difference in anatomic operation at the first and second regions, the anatomic operation derived from ultrasound data or a sensor;
   receiving signals for a plurality of laterally spaced locations in response to each of the first and second beams, sets of signals being received for each of the laterally spaced locations due to the repetition of the transmitting;
   performing spectral analysis of the signals of each set separately for each of the laterally spaced locations;
   wherein the repeating of the transmissions of the first and second beams to the first and second regions is performed such that the receiving and performing occurs in a time-continuous manner; and
   automatically adjusting the repetitions of the transmitting and repetition of the receiving to account for change in location of the first region over time, the adjusting being as a function of ultrasound data from a previous performance of the spectral analysis.

2. The non-transitory computer readable storage medium of claim 1 wherein transmitting to the first region comprises transmitting the first beams with third beams simultaneously to laterally spaced locations in the first region, wherein receiving comprises receiving along a plurality of scan lines in response to each of the simultaneous first and third beams, and wherein performing spectral analysis comprises performing spectral analysis separately for the laterally spaced locations on respective scan lines.

3. The non-transitory computer readable storage medium of claim 1 wherein the controlling is a function of a physiological cycle where the transmitting is performed for a first portion of the physiological cycle at the first region a first one of the spaced apart regions and performed for a second portion of the physiological cycle at the second region, the first and second portions comprising portions of the same physiological cycle.

4. The non-transitory computer readable storage medium of claim 1 wherein the difference in anatomic operation at the first and second regions comprises the first region being associated with greater flow than the second region during the first period, and the second region being associated with greater flow than the first region during the second period.

5. The non-transitory computer readable storage medium of claim 1 further comprising that the controlling is a function of a user input of a parameter to be measured with the spectral analysis.

6. In a non-transitory computer readable storage medium having stored therein data representing instructions executable by a programmed processor for acquiring spatially distinct Spectral Doppler information, the storage medium comprising instructions for:
   transmitting a sequence of first beams to a first region spaced apart from a second region, the sequence of the first beams being transmitted during a first period of time;
   transmitting a sequence of second beams to the second region during a second period of time different than the first period;
   repeating the transmitting of the sequences of the first and second beams;
   controlling the repeating so that the transmissions to the first region are at different times than the transmissions to the second region based on a difference in anatomic operation at the first and second regions, the anatomic operation derived from ultrasound data or a sensor;
   receiving signals for a plurality of laterally spaced locations in response to each of the first and second beams, sets of signals being received for each of the laterally spaced locations due to the repetition of the transmitting;
   performing spectral analysis of the signals of each set separately for each of the laterally spaced locations;
   wherein the repeating of the transmissions of the first and second beams to the first and second regions is performed such that the receiving and performing occurs in a time-continuous manner; and
   determining locations of the first and second regions for the transmitting by motion pattern recognition from ultrasound data.

* * * * *